United States Patent [19]

Pearlman

[11] 4,391,795

[45] Jul. 5, 1983

[54] ASSAY FOR FREE THYROID HORMONE

[75] Inventor: Samuel R. Pearlman, Union, N.J.

[73] Assignee: Becton Dickinson and Company, Paramus, N.J.

[21] Appl. No.: 131,934

[22] Filed: Mar. 21, 1980

[51] Int. Cl.$^3$ ............... G01N 33/56; G01N 33/58; G01N 33/60

[52] U.S. Cl. ........................................ 424/1; 436/500

[58] Field of Search ..................... 424/1, 12; 23/230 B

[56] References Cited

U.S. PATENT DOCUMENTS

| 4,046,870 | 9/1977 | Hertl et al. | 424/1 |
|---|---|---|---|
| 4,225,574 | 9/1980 | Romelli et al. | 424/1 |
| 4,235,865 | 11/1980 | Thoma | 424/1 |
| 4,252,782 | 2/1981 | Bailey | 424/1 |
| 4,279,885 | 7/1981 | Reese | 424/1 |

Primary Examiner—Christine M. Nucker
Attorney, Agent, or Firm—Elliot M. Olstein; Louis E. Marn

[57] ABSTRACT

Sample containing free and bound thyroid hormone; in particular, thyroxine, is contacted with immobilized binder; in particular, supported on a solid support, to bind the free thyroxine. After separating the bound thyroxine from the immobilized binder having free thyroxine bound thereto, the immobilized binder is contacted with labeled thyroxine; in particular, radiolabeled thyroxine. Unbound labeled thyroxine is removed, and the amount of bound and/or unbound labeled thyroxine is measured, with the free thyroxine concentration in the sample being inversely proportional to the amount of labeled thyroxine bound to the immobilized binder.

16 Claims, No Drawings

ASSAY FOR FREE THYROID HORMONE

This invention relates to an assay for thyroid hormones, and in particular to an assay for measuring the concentration of free thyroid hormones ($T_3$ or $T_4$) in a sample.

Thyroid hormones, such as thyroxine ($T_4$) is found in serum as free $T_4$ and as bound $T_4$. In its bound form, $T_4$ is conjugated with thyroxine binding proteins; in particular, thyroxine binding globulin.

The determination of the concentration of free $T_4$ in serum is generally considered to be useful in assessing thyroid function since free $T_4$ is the hormone made available to the tissues for hormonal action.

As a result, assays have been developed for determining the amount of free $T_4$. As representative examples of such assays, there may be mentioned the assays disclosed in U.S. Pat. Nos. 3,941,564; 3,960,492; and 4,046,870.

In accordance with the present invention, there is provided an improved method for measuring the concentration of free thyroid hormone ($T_3$ or $T_4$) in a fluid sample, wherein the free hormone is directly measured. More particularly, in accordance with the present invention, a sample, such as a serum sample, which contains free thyroid hormone as well as thyroid hormone bound to serum proteins is contacted with an immobilized binder for the free thyroid hormone, with such binder preferably being an antibody. As a result of such contact, the free hormone present in the serum sample becomes bound to the immobilized binder. After separation of the immobilized binder, which now contains the free thyroid hormone bound thereto, from the bound throid hormone present in the sample, the immobilized binder is contacted with labeled thyroid hormone in an amount which is in excess of the remaining binding sites on the immobilized binder. After separation of the bound and unbound labeled thyroid hormone, the amount of the bound and/or unbound labeled thryoid hormone is measured to thereby determine the amount of free thyroid hormone which was present in the sample, with the amount of labeled thyroid hormone bound to the immobilized binder being inversely proportional to the amount of free thyroid hormone present in the sample.

In accordance with another aspect of the invention, there is provided a kit for the assay of free thyroid hormone which includes immobilized binder for free thyroid hormone having a number of binding sites in excess of that required to bind all of the free thyroid hormone in a standard or a sample to be assayed; labeled thyroid hormone; and thyroid hormone standards of different thyroid hormone concentrations. Each of the thyroid hormone standards are preferably provided in an amount of from 50 to 200 $\mu$l. The labeled thyroid hormone is provided in an amount which exceeds the amount which can be bound by the immobilized binder after contact with a thyroid hormone standard or sample. In accordance with a preferred embodiment, the thyroid hormone standards; in particular $T_4$, are provided at different free thyroid hormone concentrations over a range of from 0 to 6.2 ng/dl.

The kit generally also includes a suitable incubation buffer.

The binder for thyroid hormone may be any one of a wide variety of binders which are known in the art. Thus, for example, the binder may be a naturally occurring binder or an antibody specific to the thyroid hormone to be assayed, with an antibody being preferred. The antibody may be produced by procedures generally known in the art. In view of the fact that the production of antibody to thyroid hormone is well known in the art, no further details in this respect are deemed necessary for a complete understanding of the present invention.

In accordance with the present invention, the antibody is employed in the assay in an immobilized form, and in particular, such antibody is supported on a solid support. The solid support may be any one of a wide variety of solid supports generally employed in a solid phase assay, and may be employed in a wide variety of forms, such as in sheet form, in particulate form, as a test tube, and the like.

As representative examples of suitable materials which can be employed as solid supports, there may be mentioned: various polymers, such as polystyrene, polyethylene, polypropylene, polyamides, polyacrylamides, and the like; red blood cells; glass beads; cellulose, dextran, and the like. In view of the fact that such solid supports are well known in the art, no details in this respect are deemed necessary for a complete understanding of the present invention.

As generally known in the art, the binder; in particular, an antibody, is generally supported on the solid support by covalent coupling through a suitable coupling agent or by activation of the support material. Thus, for example, U.S. Pat. No. 3,555,143 discloses a method for covalently binding a binder to water insoluble polymer; in particular, dextran. It is to be understood that other agents for covalent coupling are also possible within the spirit and scope of the present invention, and in view of the fact that such agents are well known in the art, no further details in this respect are needed for a complete understanding of the present invention.

It is also to be understood that the binder may be supported on a solid support by adsorption. Thus, as known in the art, binders can be adsorbed onto a polymer, such as polypropylene, and in particular, it is preferred to adsorb the binder onto a tube; e.g., as formed from polypropylene. The supporting of a binder onto a solid surface by adsorption is well known in the art, and as a result, no further details in this respect are deemed necessary for a complete understanding of the present invention.

The present invention is of particular applicability to an assay for free $T_4$.

Thus, in accordance with a preferred embodiment of the present invention, the assay for free $T_4$ is conducted by use of a $T_4$ antibody supported on a plastic tube. In conducting the assay, serum or standard sample is contacted with the $T_4$ binder on a solid support for a time sufficient to bind the free $T_4$ present in the serum or sample. Thus, in accordance with the present invention, the serum is not pretreated to free $T_4$ from endogenous proteins, and as a result, the free $T_4$ present in the serum sample, as opposed to $T_4$ bound to endogenous protein, is bound to the immobilized binder.

The serum sample is then separated from the immobilized binder, and the immobilized binder is then contacted with a $T_4$ tracer; i.e., labeled $T_4$, preferably radiolabeled $T_4$, and most preferably $^{125}I$ labeled $T_4$. The remaining binding sites of the immobilized binder are then saturated by the $T_4$ tracer, and the excess tracer is removed. The amount of $T_4$ tracer which becomes bound to the immobilized binder is inversely proportional to the amount of free $T_4$ present in the serum or standard sample. Thus, by determining the amount of tracer which is bound to the immobilized binder, the amount of free $T_4$ present in the serum sample can be determined.

As known in the art, the amount of free $T_4$ present in a serum sample is determined by comparing the amount of $T_4$ tracer bound to the immobilized binder with a standard curve prepared by procedures known in the art.

The present invention will be further described with respect to the following example; however, the scope of the invention is not to be limited thereby:

EXAMPLE

The following reagent kit is used in the Free $T_4$ Radioassay:
1. Incubation Buffer—0.075 M sodium barbital, pH 8.6, or 0.05 M Tris chloride, pH 7.6.
2. $T_4$ Tracer Solution—9 $\mu$Ci thyroxine [$^{125}$I] in 110 ml barbital buffer, pH 8.6, containing 8anilino-1-naphthalene sulfuric acid (ANS).
3. $T_4$ Antibody-Coated Tubes—plastic tubes coated with $T_4$ antiserum.
4. Free $T_4$ Serum Standards A-F—human serum with L-thyroxine added and calibrated to give the following $FT_4$ levels:

| Standard | $FT_4$, ng/dl |
|---|---|
| A | 0 |
| B | 0.3 |
| C | 0.8 |
| D | 1.2 |
| E | 4.5 |
| F | 6.2 |

The assay procedure is as follows:
1. Number 12 tubes for the standard curve. Beginning with 13, number two tubes for each clinical sample.
2. Add $FT_4$ Serum Standards and samples as follows:

| Tube No. | $FT_4$ Standard | $FT_4$ ng/dl |
|---|---|---|
| 1,2 | 200 $\mu$l A* | 0 |
| 3,4 | 200 $\mu$l B | 0.3 |
| 5,6 | 200 $\mu$l C | 0.8 |
| 7,8 | 200 $\mu$l D | 1.2 |
| 9,10 | 200 $\mu$l E | 4.5 |
| 11,12 | 200 $\mu$l F | 6.2 |
| 13,14 | 200 $\mu$l clinical sample | To be determined |

*This volume (A-F and clinical samples) can be as low as 50 $\mu$l.

3. Add 1.0 ml of incubation buffer to each tube. Gently mix each tube.
4. Incubate at room temperature (>18° C.) for 30 minutes or in a water bath at 37±1° C. for 30 minutes from the time of the last addition in the previous step. Place all tubes, standards and samples, in the bath at the same time.
5. At the end of the required time for incubation, aspirate or decant all tubes.
6. Add 1.0 ml distilled or deionized water to all tubes. This is rinsed down the side of each tube.
7. Reaspirate or decant all tubes.
8. Add 1.0 ml of $T_4$ tracer solution to each tube. Gently mix each tube.
9. Incubate at room temperature for 30 minutes.
10. Aspirate or decant the tracer solution from each tube.
11. Add 1.0 ml distilled or deionized water to all tubes. This is rinsed down the side of each tube.
12. Reaspirate or decant all tubes. The tubes now contain labeled and unlabeled $T_4$ bound to antibody.
13. Count the radioactivity in the tubes in sequence for the same length of time with a solid crystal scintillation counter. Counting data for an assay using 200 $\mu$l aliquots of standards (and samples) and barbital buffer in the first incubation step, 30 minutes at 37° C., are as follows:

| Tube No. | Counts per Minute | % of Average Trace Level | $FT_4$ ng/dl |
|---|---|---|---|
| 1 | 22832 | — | Trace Level |
| 2 | 23111 | — | Trace Level |
| 3 | 19983 | 86.9 | 0.3 |
| 4 | 19572 | 85.2 | 0.3 |
| 5 | 17694 | 77.0 | 0.8 |
| 6 | 17685 | 76.9 | 0.8 |
| 7 | 15611 | 67.9 | 1.2 |
| 8 | 15365 | 66.8 | 1.2 |
| 9 | 11610 | 50.5 | 4.5 |
| 10 | 11079 | 48.2 | 4.5 |
| 11 | 8801 | 38.3 | 6.2 |
| 12 | 8801 | 38.3 | 6.2 |

Similar counting data have been obtained when 50 $\mu$l aliquots of standards (and samples) and tris buffer were taken in the first incubation step, 30 minutes at room temperature.

Sample calculations for a patient serum are as follows:
1. Using semi-log paper, counts per minute are plotted against ng/dl $FT_4$ standard on the log scale; or using logit-log paper, % of average trace level is plotted against ng/dl $FT_4$ standard on the log scale.
2. The concentration of $FT_4$ in a patient serum is determined by interpolation from a standard curve. For example, a serum sample assayed in duplicate along with the standards, for which data are tabulated above, gave counts per minute of 13521 and 13791 (corresponding to % of average trace level of 58.8 and 60.0%). The $FT_4$ values calculated from the standard curve were 2.26 and 2.12 ng/dl, respectively, for an average value of 2.19 ng/dl.

The present invention is particularly advantageous in that free $T_4$ can be easily determined. The method directly evaluates the free $T_4$ in a serum sample by a fast sensitive procedure, and in fact, such procedure can be accomplished by the use of 200 $\mu$l or less; e.g., as low as 50 $\mu$l, sample per tube. The methods generally employed for determining free $T_4$ such as by equilibrium dialysis requires 0.5 to 1.0 ml per tube and several days.

As known in the art, the free $T_4$ assay is useful for determination of hyperthyroid, euthyroid and hypothyroid conditions.

Numerous modifications and variations of the present invention are possible in light of the above teachings and, therefore, within the scope of the appended claims, the invention may be practised otherwise than as particularly described.

I claim:
1. A process for determining free thyroid hormone in a serum sample, comprising:
introducing a serum sample containing free thyroid hormone and thyroid hormone bound to serum proteins into a tube coated with a binder for free thyroid hormone, said binder having a number of binding sites in excess of that required to bind all of the free thyroid hormone in the serum sample, said serum sample containing the free and bound thyroid hormone being in contact with said binding sites;

incubating said serum sample in said tube to bind free thyroid hormone to said binder;

removing from the tube the serum sample which is not bound to said coated binder;

thereafter introducing into said tube labelled thyroid hormone in an amount in excess of the remaining binding sites of the coated binder to bind a portion of the labelled thyroid hormone to the coated binder;

removing from the tube unbound labelled thyroid hormone; and measuring the amount of at least one of the bound and unbound labelled thyroid hormone for determining the amount of free thyroid hormone present in the serum sample.

2. The process of claim 1 wherein the binder is an antibody.

3. The process of claim 2 wherein the labeled thyroid hormone is radiolabeled.

4. The process of claim 3 wherein the label is radioiodine.

5. The process of claim 4 wherein the sample amount is from 50 to 200 μl.

6. The process of claim 1 wherein the thyroid hormone is $T_4$.

7. The process of claim 6 wherein the binder is an antibody.

8. The process of claim 7 wherein the labeled $T_4$ hormone is radiolabeled.

9. The process of claim 8 wherein the label is radioiodine.

10. The process of claim 9 wherein the sample amount is from 50 to 200 μl.

11. A kit for determining free thyroid hormone in a serum sample, comprising:

a tube coated with a binder for free thyroid hormone, said binder having a number of binding sites in excess of that required to bind all of the free thyroid hormone in a thyroid hormone standard or serum sample containing free thyroid hormone and thyroid hormone bound to serum protein which is in contact with the binding sites;

labelled thyroid hormone in an amount in excess of that required for saturating all of the binding sites after contact with the standard or serum samples; and thyroid hormone standards of different thyroid hormone concentrations.

12. The kit of claim 11 wherein each of the thyroid standards is provided in an amount of from 50 to 200 μl.

13. The kit of claim 12 wherein the labeled thyroid hormone is radioiodine labeled thyroid hormone.

14. The kit of claim 13 wherein the thyroid hormone standards are provided with different thyroid hormone concentrations over a range of from 0 to 6.2 ng/dl.

15. The kit of claim 11 wherein the thyroid hormone is $T_4$.

16. The kit of claim 13 wherein the thyroid hormone is $T_4$.

* * * * *